United States Patent [19]

Franke et al.

[11] Patent Number: 4,571,409

[45] Date of Patent: Feb. 18, 1986

[54] AMINOPROPANOL DERIVATIVES OF 2-HYDROXY-β-PHENYL-PROPIOPHENONES, THEIR PREPARATION AND THERAPEUTIC AGENTS CONTAINING THESE COMPOUNDS

[75] Inventors: Albrecht Franke, Wachenheim; Josef Mueller, Ludwigshafen; Helmut Lietz, Neustadt; Walter-Wielant Wiersdorff, Mutterstadt; Hans-Guenther Hege, Neustadt; Claus D. Mueller, Viernheim; Josef Gries, Wachenheim; Dieter Lenke, Ludwigshafen; Gerda von Philipsborn, Weinheim; Manfred Raschack, Weisenheim am Sand, all of Fed. Rep. of Germany

[73] Assignee: BASF Aktiengesellschaft, Fed. Rep. of Germany

[21] Appl. No.: 733,631

[22] Filed: May 13, 1985

Related U.S. Application Data

[60] Division of Ser. No. 613,389, May 23, 1984, which is a continuation of Ser. No. 416,228, Sep. 9, 1982, abandoned.

[30] Foreign Application Priority Data

Sep. 18, 1981 [DE] Fed. Rep. of Germany ....... 3137178
Jul. 17, 1982 [DE] Fed. Rep. of Germany ....... 3226863

[51] Int. Cl.$^4$ ..................... A61K 31/135; C07C 97/10
[52] U.S. Cl. ..................................... 514/652; 564/349
[58] Field of Search ......................................... 564/349

[56] References Cited

U.S. PATENT DOCUMENTS 4,460,605 7/1984 Petrik et al. ......................... 564/349

FOREIGN PATENT DOCUMENTS 1307455 2/1973 United Kingdom .

Primary Examiner—Robert W. Ramsuer
Attorney, Agent, or Firm—Keil & Weinkauf

[57] ABSTRACT

Novel aminopropanol derivatives of 2-hydroxy-β-phenyl-propiophenones and their physiologically acceptable acid addition compounds, processes for their preparation and therapeutic agents which contain these derivatives and are useful as antiarrhythmic drugs.

6 Claims, No Drawings

AMINOPROPANOL DERIVATIVES OF 2-HYDROXY-β-PHENYL-PROPIOPHENONES, THEIR PREPARATION AND THERAPEUTIC AGENTS CONTAINING THESE COMPOUNDS

This is a division of application Ser. No. 613,389, filed May 23, 1984, which is a continuation of application Ser. No. 416,228, filed Sept. 9, 1982, abandoned.

The present invention relates to novel aminopropanol derivatives of 2-hydroxy-β-phenyl-propiophenones and their physiologically acceptable acid addition compounds, processes for their preparation and therapeutic agents which contain these derivatives and are useful as antiarrhythmic drugs.

German Laid-Open Application DOS No. 2,001,431 discloses that the n-propylamino-, n-butylamino, sec.-butylamino- and tert.-butylamino-propanol derivatives of 2-hydroxy-β-phenyl-propiophenone have an antiarrhythmic action. This is particularly true of 2-(2'-hydroxy-3'-n-propylamino-propoxy)-β-phenyl-propiophenone hydrochloride, which is known as an antiarrhythmic under the name propafenone.

It is an object of the present invention to provide better antiarrhythmic drugs than these.

We have found that this object is achieved by aminopropanol derivatives of 2-hydroxy-β-phenyl-propiophenones, of the formula I

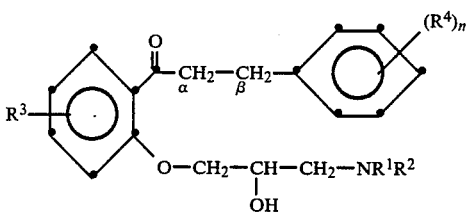

where $R^1$ and $R^2$ are identical or different and each is hydrogen, alkyl, cycloalkyl, alkenyl, alkynyl or hydroxyalkyl of in each case not more than 6 carbon atoms, alkoxyalkyl, alkylthioalkyl or dialkylaminoalkyl of in each case not more than 9 carbon atoms, or phenylalkyl or phenoxyalkyl, where alkyl is of not more than 6 carbon atoms and the phenyl is unsubstituted or substituted by alkyl or alkoxy of in each case not more than 3 carbon atoms, or $R^1$ and $R^2$, together with the nitrogen atom linking them, are a 5- to 7-membered saturated heterocyclic ring, which is unsubstituted or substituted by one or two phenyl and/or hyroxyl radicals and may contain oxygen or nitrogen as a further hetero-atom in the ring, in which case an additional nitrogen atom may be substituted by alkyl of 1 to 3 carbon atoms or phenyl, $R^3$ is hydrogen, alkyl of not more than 3 carbon atoms, fluorine, chlorine, bromine, hydroxyl or alkoxy of not more than 6 carbon atoms, $R^4$ is hydrogen, alkyl of not more than 3 carbon atoms, fluorine, chlorine, bromine, alkoxy of not more than 3 carbon atoms or $NR^5R^6$, where $R^5$ and $R^6$ are identical or different and each is alkyl of not more than 6 carbon atoms, or $R^5$ and $R^6$, together with the nitrogen atom linking them, are a heterocyclic ring, but where $R^1$, $R^3$ and $R^4$ cannot all be hydrogen if $R^2$ is alkyl of 3 or 4 carbon atoms, and n is 1, 2 or 3, and physiologically acceptable acid addition salts thereof, which have useful pharmacological properties.

Compounds of the formula I where $R^3$ is hydrogen and n is 1 or 2 are particularly noteworthy. $NR^1R^2$ is preferably a piperidine, piperazine, N-methylpiperazine, morpholine or diisopropylamino radical. Examples of $R^1$ and $R^2$ are propyl, butyl, alkoxyalkyl and hydroxyalkyl, such as n-propyl, isopropyl, n-butyl, isobutyl, tert.-butyl, methoxymethyl, methoxyethyl, hydroxymethyl and hydroxyethyl. $R^4$ is preferably hydrogen, $C_1$-$C_4$-alkoxy, dimethylamino or diethylamino.

Specific compounds, in addition to those in the Examples, are: 2-[2'-hydroxy-3'-(2-hydroxyethylamino)-propoxy]-β-phenyl-propiophenone, 2-[2'-hydroxy-3'-(2-ethoxyethylamino)-propoxy]-β-phenyl-propiophenone, 2-[2'-hydroxy-3'-(2-n-propoxy-1-methylethylamino)-propoxy]-β-phenyl-propiophenone, 2-(2'-hydroxy-3'-propargylamino-propoxy)-β-phenyl-propiophenone, 2-[2'-hydroxy-3'-(4-hydroxybutylamino)-propoxy]-β-phenyl-propiophenone, 2-(2'-hydroxy-3'-di-n-propylamino-propoxy)-β-phenyl-propiophenone, 2-[2'-hydroxy-3'-(N-methyl-N-propylamino)-propoxy]-β-phenyl-propiophenone, 2-(2'-hydroxy-3'-pyrrolidino-propoxy)-β-phenyl-propiophenone, 2-(2'-hydroxy-3'-cyclobutylamino-propoxy)-β-phenyl-propiophenone, 2-(2'-hydroxy-3'-cyclopentylamino-propoxy)-β-phenyl-propiophenone, 2-[2'-hydroxy-3'-(1-methyl-2-phenylethylamino)propoxy]-β-phenyl-propiophenone, 2-[2'-hydroxy-3'-(2-diethylaminoethylamino)propoxy]-β-phenyl-propiophenone, 2-[2'-hydroxy-3'-(3-diethylaminopropylamino)-propoxy]-β-phenyl-propiophenone, 2-[2'-hydroxy-3'-(2-piperidinoethylamino)-propoxy]-β-phenyl-propiophenone, 2-[2'-hydroxy-3'-(2-morpholinoethylamino)-propoxy]-β-phenyl-propiophenone, 2-[2'-hydroxy-3'-(4-ethyl-1-piperazino)-propoxy]β-phenyl- propiophenone, 2-[2'-hydroxy-3'-(2-methylaminoethylamino)propoxy]-β-phenyl-propiophenone, 2-[2'-hydroxy-3'-(3-hydroxy-piperidino)-propoxy]-β-phenyl-propiophenone, 2-[2'-hydroxy-3'-(4-phenyl-piperidino)-propoxy]-β-phenyl-propiophenone, 2-[2'-hydroxy-3'-(4-hydroxy-4-p-chlorophenyl-piperidino)-propoxy]-β-phenyl-propiophenone, 2-(2'-hydroxy-3'-n-propylamino-propoxy)-5-methyl-β-phenyl-propiophenone, 2-(2'-hydroxy-3'-n-butylamino-propoxy)-5-methyl-β-phenyl-propiophenone, 2-(2'-hydroxy-3'-isopropylamino-propoxy)-5-methyl-β-phenyl-propiophenone, 2-(2'-hydroxy-3'-tert.-butylamino-propoxy)-5-methyl-β-phenyl-propiophenone, 2-[2'-hydroxy-3'-(2-methoxyethylamino)-propoxy]-5-methyl-β-phenyl-propiophenone, 2-[2'-hydroxy-3'-(4-hydroxybut-2-yl-amino)-propoxy]-5methyl-β-phenyl-propiophenone, 2-[2'-hydroxy-3'-(4-hydroxy-4-phenyl-piperidino)-propoxy]-5-methyl-β-phenyl-propiophenone, 2-(2'-hydroxy-3'-piperidino-propoxy)5-methyl-β-phenyl-propiophenone, 2-(2'-hydroxy-3'-n-propylamino-propoxy)-4-methyl-β-phenyl- propiophenone, 2-(2'-hydroxy-3'-n-butylamino-propoxy)-4-methyl-β-phenyl-propiophenone, 2-(2'-hydroxy-3'-isopropylamino-propoxy)-4-methyl-β-phenyl-propiophenone, 2-(2'-hydroxy-3'-tert.-butylamino-propoxy)-4-methyl-β-phenyl-propiophenone, 2-[2'-hydroxy-3'-(2-methoxyethylamino)propoxy]-4-methyl-β-phenyl-propiophenone, 2-[2'-hydroxy-3'-(4-hydroxybut-2-ylamino)-propoxy]-4-methyl-β-phenyl-propiophenone, 2-[2'-hydroxy-3'-(4-hydroxy-4-phenyl-piperidino)-propoxy]-4-methyl-β-phenyl-propiophenone, 2-(2'-hydroxy-3'-piperidino-propoxy)-4-methyl-β-phenyl-propiophenone, 2-(2'-hydroxy-3'-n-propylamino-propoxy)-5- methoxy-β-phenyl-propiophenone, 2-(2'-hydroxy-3'-n-butylamino-propoxy)-5-methoxy-β-phenyl-propiophenone, 2-(2'-hydroxy-3'-isopropylaminopropoxy)-5-methoxy-β-phenyl-propiophenone, 2-(2'-hydroxy-3'-tert.-butylamino-propoxy)-5-methoxy-β-phenyl-propiophenone, 2-[2'-hydroxy-3'-(2-methoxyethylamino)-propoxy]-5-methoxy-β-phenyl-propiophenone, 2-[2'-hydroxy-3'-(4-hydroxybut-2-ylamino)-propoxy]-5-methoxy-β-phenyl-propiophenone, 2-[2'-hydroxy-3'-(4-hydroxy-4-phenyl-piperidino)-propoxy]-5-methoxy-β-phenyl-propiophenone, 2-(2'-hydroxy-3'-piperidino-propoxy)-5-methoxy-β-phenyl-propiophenone, 2-(2'-hydroxy-3'-n-propylamino-propoxy)-5-fluoro-β-phenyl-propiophenone, 2-(2'-hydroxy-3'-n-butylamino-propoxy)-5-fluoro-β-phenyl-propiophenone, 2-(2'-hydroxy-3'-isopropylamino-propoxy)-5-fluoro-β-phenyl-propiophenone, 2-(2'-hydroxy-3'-tert.-butylamino-propoxy)-5-fluoro-β-phenyl-propiophenone, 2-[2'-hydroxy-3'-(2-methoxyethylamino)-propoxy]-5-fluoro-β-phenyl-propiophenone, 2-[2'-hydroxy-3'-(4-hydroxybut-2-ylamino)-propoxy]-5-fluoro-β-phenyl-propiophenone, 2-[2'-hydroxy-3'-(4-hydroxy-4-phenyl-piperidino)-propoxy]-5-fluoro-β-phenyl-propiophenon, 2-(2'-hydroxy-3'-piperidino-propoxy)-5-fluoro-β-phenyl-propiophenone, 2-(2'-hydroxy-3'-n-propylamino-propoxy)-4-fluoro-β-phenyl-propiophenone, 2-(2'-hydroxy-3'-n-butylamino-propoxy)-4-fluoro-β-phenyl-propiophenone, 2-(2'-hydroxy-3'-isopropylamino-propoxy)-4-fluoro-β-phenyl-propiophenone, 2-(2'-hydroxy-3'-tert.-butylamino-propoxy)-4-fluoro-β-phenyl-propiophenone, 2-[2'-hydroxy-3'-(2-methoxyethylamino)propoxy]-4-fluoro-β-phenyl-propiophenone, 2-[2'-hydroxy- 3'-(4-hydroxybut-2-ylamino)-propoxy]-4-fluoro-β-phenyl-propiophenone, 2-[2'-hydroxy-3'-(4-hydroxy-4-phenyl-piperidino)-propoxy]-4-fluoro-β-phenyl-propiophenone, 2-(2'-hydroxy-3'-piperidino-propoxy)-4-fluoro-β-phenyl-propiophenone, 2-(2'-hydroxy-3'-n-propylamino-propoxy)-4-chloro-β-phenyl-propiophenone, 2-(2'-hydroxy-3'-n-butylamino-propoxy)-4-chloro-β-phenyl-propiophenone, 2-(2'-hydroxy-3'-isopropylamino-propoxy)-4-chloro-β-phenyl-propiophenone, 2-(2'-hydroxy-3'-tert.-butylamino-propoxy)-4-chloro-β-phenyl-propiophenone, 2-[2'-hydroxy-3'-(2-methoxyethylamino)-propoxy]-4-chloro-β-phenyl-propiophenone, 2-[2'-hydroxy-3'-(4-hydroxybut-2-ylamino)-propoxy]-4-chloro-β-phenyl-propiophenone, 2-[2'-hydroxy-3'-(4-hydroxy-4-phenyl-piperidino)-propoxy]-4-chloro-β-phenyl-propiophenon, 2-(2'-hydroxy-3'-piperidino-propoxy)-4-chloro-β-phenyl-propiophenone, 2-(2'-hydroxy-3'-n-propylamino-propoxy)-5-n-propoxy-β-phenyl-propiophenone, 2-(2'-hydroxy-3'-n-butylamino-propoxy)-5-n-propoxy-β-phenyl-propiophenone, 2-(2'-hydroxy-3'-isopropylamino-propoxy)-5-n-propoxy-β-phenyl-propiophenone, 2-(2'-hydroxy-3'-tert.-butylamino)propoxy)-5-n-propoxy-β-phenyl-propiophenone, 2-[2'-hydroxy-3'-(2-methoxyethylamino)-propoxy]-5-n-propoxy-β-phenyl-propiophenone, 2-[2'-hydroxy-3'-(4-hydroxybut-2-yl-amino)-propoxy]-5-n-propoxy-β-phenyl-propiophenone, 2-[2'-hydroxy-3'-(4-hydroxy-4-phenyl-piperidino)-propoxy]-5-n-propoxy-β-phenyl-propiophenone, 2-(2'-hydroxy-3'-piperidino-propoxy)-5-n-propoxy-β-phenyl-propiophenone, 2-(2'-hydroxy-3'-n-propylamino-propoxy)-5-n-propyl-β-phenyl-propiophenone, 2-(2'-hydroxy-3'-n-butylamino-propoxy)-5-n-propyl-β-phenyl-propiophenone, 2-(2'-hydroxy-3'-isopropylamino-propoxy)-5-n-propyl-β-phenyl-propiophenone, 2-(2'-hydroxy-3'-tert.-butylamino-propoxy)-5-n-propyl-β-phenyl-propiophenone, 2-[2'-hydroxy-3'-(2-methoxyethylamino)-propoxy]-5-n-propyl-β-phenyl-propiophenone, 2-[2'-hydroxy-3'-(4-hydroxybut-2-ylamino)-propoxy]-5-n-propyl-β-phenyl-propiophenone, 2-[2'-hydroxy-3'-(4-hydroxy-4-phenyl-piperidino)-propoxy]-5-n-propyl-β-phenyl-propiophenone, 2-(2'-hydroxy-3'-piperidino-propoxy)-5-n-propyl-β-phenyl-propiophenone, 2-(2'-hydroxy-2'-n-propylaminopropoxy)-4-n-butyl-β-phenyl-propiophenone, 2-(2'-hydroxy-3'-n-butylamino-propoxy)-4-n-butyl-β-phenyl-propiophenone, 2-(2'-hydroxy-3'-isopropylamino-propoxy)-4-n-butyl-β-phenyl-propiophenone, 2-(2'-hydroxy-3'-tert.-butylaminopropoxy)-4-n-butyl-β-phenyl-propiophenone, 2-[2'-hydroxy-3'-(2-methoxyethylamino)-propoxy]-4-n-butyl-β-phenyl-propiophenone, 2-[2'-hydroxy-3'-(4-hydroxybut-2-ylamino)propoxy]-4-n-butyl-β-phenyl-propiophenone, 2-[2'-hydroxy-3'-(4-hydroxy-4-phenyl-piperidino)-propoxy]-4-n-butyl-β-phenyl-propiophenone, 2-(2'-hydroxy-3'-piperidino-propoxy)-4-n-butyl-β-phenyl-propiophenone, 2-(2'-hydroxy-3'-n-butylamino-propoxy)-4-hydroxy-β-phenyl-propiophenone, 2-(2'-hydroxy-3'-isopropylamino-propoxy)-4-hydroxy-β-phenyl-propiophenone, 2-(2'-hydroxy-3'-tert.-butylamino-propoxy)-4-hydroxy-β-phenyl-propiophenone, 2-[2'-hydroxy-3'-(2-methoxyethylamino)-propoxy]-4-hydroxy-β-phenyl-propiophenone, 2-[2'-hydroxy-3'-(4-hydroxybut-2-ylamino)-propoxy]-4-hydroxy-β-phenyl-propiophenone, 2-[2'-hydroxy-3'-(4-hydroxy-4-phenyl-piperidino)-propoxy]-4-hydroxy-β-phenyl- propiophenone, 2-(2'-hydroxy-3'-piperidino-propoxy)-4-hydroxy-β-phenyl-propiophenone, 2-(2'-hydroxy-3'-n-butylamino-propoxy)-5-hydroxy-β-phenyl-propiophenone, 2-(2'-hydroxy-3'-isopropylamino-propoxy)-5-hydroxy-β-phenyl-propiophenone, 2-(2'-hydroxy-3'-tert.-butylamino-propoxy)-5-hydroxy-β-phenyl-propiophenone, 2-[2'-hydroxy-3'-(2-methoxyethylamino)-propoxy]-5-hydroxy-β-phenyl-propiophenone, 2-[2'-hydroxy-3'-(4-hydroxybut-2-ylamino)-propoxyl-5-hydroxy-β-phenyl-propiophenone, 2-[2'-hydroxy-3'-(4-hydroxy-4-phenyl-piperidino)-propoxy]-5-hydroxy-β-phenyl-propiophenone, 2-[2'-hydroxy-3'-piperidino-propoxy]-5-hydroxy-β-phenyl-propiophenone, 2-(2'-hydroxy-3'-n-propylamino-propoxy)β-(2-methyl-phenyl)-propiophenone, 2-(2'-hydroxy-3'-n-butylamino-propoxy)-β-(2-methyl-phenyl)-propiophenone, 2-(2'-hydroxy-3'-isopropylamino-propoxy)-β-(2-methyl-phenyl)-propiophenone, 2-(2'-hydroxy-3'-tert.-butylamino-propoxy)-β-(2-methyl-phenyl)-propiophenone, 2-[2'-hydroxy-3'-(2-methoxyethylamino)-propoxy]-β-(2-methylphenyl)-propiophenone, 2-[2'-hydroxy-3'-(4-hydroxy-but-2-ylamino)-propoxy]-β-(2-methylphenyl)-propiophenone, 2-[2'-hydroxy-3'-(4-hydroxy-4-phenyl-piperidino)-propoxy]-β-(2-methylphenyl)-propiophenone, 2-(2'-hydroxy-3'-piperidino-propoxy)-β-(2-methylphenyl)-propiophenone, 2-(2'-hydroxy-3'-n-propylamino-propoxy)-β-(3-methoxyphenyl)-propiophenone, 2-(2'-hydroxy-3'-n-butylamino-propoxy)-β-(3-methoxyphenyl)-propiophenone, 2-(2'-hydroxy-3'-isopropylamino-propoxy)-β-(3-methoxyphenyl)-propiophenone, 2-(2'-hydroxy-3'-tert.-butylamino-propoxy)-β-(3-methoxyphenyl)-propiophenone, 2-[2'-hydroxy-3'-(2-methoxyethyl amino)-propoxy]-β-(3-methoxyphenyl)-propiophenone, 2-[2'-hydroxy-3'-(4-hydroxybut-2-ylamino)-propoxy]-β-(3-methoxyphenyl)-propiophenone, 2-[2'-hydroxy-3'-(4-hydroxy-4-phenyl-piperidino)-propoxy]-β-(3-methoxyphenyl)-propiophenone, 2-(2'-hydroxy-3'-piperidino-propoxy)-β-(3-methoxyphenyl)-propiophenone, 2-(2'-hydroxy-3'-n-propylaminopropoxy)-β-(3,4-methylenedioxyphenyl)-propiophenone, 2-(2'-hydroxy-3'-n-butylamino-propoxy)-β-(3,4-methylenedioxyphenyl)-propiophenone, 2-(2'-hydroxy-3'-isopropylamino-propoxy)-β-(3,4-methylenedioxyphenyl)-propiophenone, 2-(2'-hydroxy-3'-tert.-butylamino-propoxy)-β-(3,4-methylenedioxyphenyl)-propiophenone, 2-[2'-hydroxy-3'-(2-methoxyethylamino)-propoxy]-β-(3,4-methylenedioxyphenyl)-propiophenone, 2-[2'-hydroxy-3'-(4-hydroxybut-2-ylamino)-propoxy]-β-(3,4-methylenedioxyphenyl)-propiophenone, 2-[2'-hydroxy-3'-(4-hydroxy-4-phenyl-piperidino)-propoxy]-β-(3,4-methylenedioxyphenyl)-propiophenone, 2-(2'-hydroxy-3'-piperidino-propoxy)-β-(3,4-methylenedioxyphenyl)-propiophenone, 2-(2'-hydroxy-3'-n-propylamino-propoxy)-β-(3,4-dichlorophenyl)-propiophenone, 2-(2'-hydroxy-3'-n-butylamino-propoxy)-β-(3,4-dichlorophenyl)-propiophenone, 2-(2'-hydroxy-3'-isopropylamino-propoxy)-β-(3,4-dichlorophenyl)-propiophenone, 2-(2'-hydroxy-3'-tert.-butylaminopropoxy)-β-(3,4-dichlorophenyl)-propiophenone, 2-[2'-hydroxy-3'-(2-methoxyethylamino)-propoxy]-β-(3,4-dichlorophenyl)-propiophenone, 2-[2'-hydroxy-3'-(4-hydroxybut-2-ylamino)-propoxy]-β-(3,4-dichlorophenyl)-propiophenone, 2-[2'-hydroxy-3'-(4-hydroxy-4-phenyl-piperidino)-propoxy]-β-(3,4-dichlorophenyl)-propiophenone, 2-(2'-hydroxy-3'-piperidino-propoxy)-β-(3,4-dichlorophenyl)-propiophenone, 2-(2'-hydroxy-3'-n-propylamino-propoxy)-β-(3-hydroxyphenyl)-propiophenone, 2-(2'-hydroxy-3'-n-butylaminopropoxy)-β-(3-hydroxyphenyl)-propiophenone, 2-(2'-hydroxy-3'-isopropylamino-propoxy)-β-(3-hydroxyphenyl)-propiophenone, 2-(2'-hydroxy-3'-tert.-butylamino-propoxy)-β-(3-hydroxyphenyl)-propiophenone, 2-[2'-hydroxy-3'-(2-methoxyethylamino)-propoxy]-β-(3-hydroxyphenyl)-propiophenone, 2-[2'-hydroxy-3'-(4-hydroxy-but-2-ylamino)-propoxy]-β-(3-hydroxyphenyl)-propiophenone, 2-[2'-hydroxy-3'-(4-hydroxy-4-phenyl-piperidino)-propoxy]-β-(3-hydroxyphenyl)-propiophenone, 2-(2'-hydroxy-3'-piperidino-propoxy)-β-(3-hydroxyphenyl)-propiophenone, 2-(2'-hydroxy-3'-n-propylaminopropoxy)-β-(4-hydroxyphenyl)-propiophenone, 2-(2'-hydroxy-3'-n-butylamino-propoxy)-β-(4-hydroxyphenyl)-propiophenone, 2-(2'-hydroxy-3'-isopropylamino-propoxy)-β-(4-hydroxyphenyl)-propiophenone, 2-(2'-hydroxy-3'-tert.-butylaminopropoxy)-β-(4-hydroxyphenyl)-propiophenone, 2-[2'-hydroxy-3'-(2-methoxyethylamino)-propoxy]-β-(4-hydroxyphenyl)-propiophenone, 2-[2'-hydroxy-3'-(4-hydroxybut-2-ylamino)-propoxy]-β-(4-hydroxyphenyl)-propiophenone, 2-[2'-hydroxy-3'-(4-hydroxy-4-phenyl-piperidino)-propoxy]-β-(4-hydroxyphenyl)-propiophenone, 2-(2'-hydroxy-3'-piperidino-propoxy)-β-(4-hydroxyphenyl)-propiophenone, 2-(2'-hydroxy-3'-n-propylamino-propoxy)-β-(2-dimethylaminophenyl)-propiophenone, 2-(2'-hydroxy-3'-piperidino-propoxy)-β-(2-dimethylaminophenyl)-propiophenone, 2-(2'-hydroxy-3'-n-propylamino-propoxy)-β-(3-dimethylaminophenyl)-propiophenone, 2-[2'-hydroxy-3'-(N,N-diisopropylamino)-propoxy]-β-(3-di ethylaminophenyl)-propiophenone, 2-(2'-hydroxy-3'-morpholino-propoxy)-β-(2-piperidino-phenyl)-propiophenone, 2-(2'-hydroxy-3'-n-propylamino-propoxy)-β-(4-piperdino-phenyl)-propiophenone, 2-(2'-hydroxy-3'-n-propylamino-propoxy)-β-(4-diisopropylaminophenyl)-propiophenone, 2-(2'-hydroxy-3'-n-propylamino-propoxy)-β-(4-piperidino-phenyl)-propiophenone, 2-(2'-hydroxy-3'-n-propylamino-propoxy)-5-hydroxy-β-(4-dimethylaminophenyl)-propiophenone, 2-(2'-hydroxy-3'-n-propylamino-propoxy)-5-methoxy-β-(4-diethylaminophenyl)-propiophenone and 2-(2'-hydroxy-3'-piperidino-propoxy)-5-methoxy-β-(4-piperidinophenyl)-propiophenone.

The compounds according to the invention can be prepared by a process wherein (a) a compound of the formula II

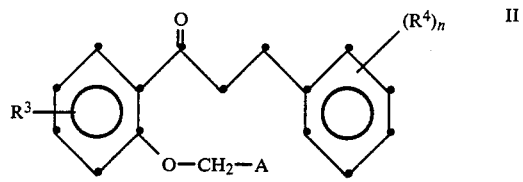

where A is

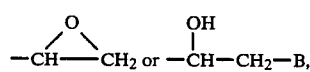

where B is a nucleofugic leaving group, and $R^3$, $R^4$ and n have the above meanings, is reacted with an amine of the formula III $HNR^1R^2$           III where $R^1$ and $R^2$ have the above meanings, or (b) a compound of the formula IV

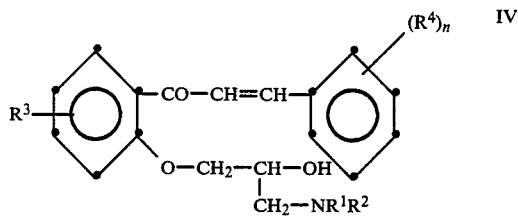

where $R^1$, $R^2$, $R^3$, $R^4$ and n have the above meanings, are subjected to catalytic hydrogenation, and, if appropriate, the compound thus obtained is converted into an acid addition salt of a physiologically acceptable acid.

In process (a), the leaving group B is preferably halogen, in particular chlorine, bromine or iodine. Examples of other suitable nucleofugic leaving groups include aromatic or aliphatic sulfonic acid radicals, such as the p-toluenesulfonic acid or methanesulfonic acid radical.

The reactions are carried out at room temperature or higher, advantageously at from 50° to 120° C., under atmospheric pressure or in a closed vessel under superatmospheric pressure, if necessary with warming.

The starting compounds can be reacted directly, i.e. without addition of a diluent or solvent. However, an inert diluent or solvent is advantageously used, for example a lower alcohol of 1 to 4 carbon atoms, such as methanol, ethanol or propanol, but preferably isopropanol or ethanol, a lower saturated dialkyl ether, dialkyl glycol ether or cyclic ether, such as diethyl ether, 1,2-dimethoxyethane, tetrahydrofuran or dioxane, benzene or an alkylbenzene, such as toluene or xylene, an aliphatic hydrocarbon, such as hexane, heptane or octane, a lower aliphatic ketone, such as acetone, methyl ethyl ketone or methyl isobutyl ketone, a dialkylformamide, such as dimethyl- or diethyl-formamide, dimethylsulfoxide, water or a mixture of the above solvents. The amine of the general formula $HNR^1R^2$ used in excess may also be suitable as the diluent or solvent.

Preferred solvents for the reaction of the compounds II

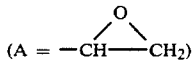
(A = —CH——CH$_2$)

with an amine HNR$^1$R$^2$ are lower alcohols, in particular ethanol or isopropanol, and the reaction is preferably carried out at from 50° to 120° C. and under atmospheric pressure.

Completion of the reaction depends on the reaction temperature, and is generally achieved within from 1 to 15 hours. The product can be isolated in a conventional manner, for example by filtration or by distilling off the diluent or solvent from the reaction mixture. The resulting compound is pruified in a conventional manner, for example by recrystallization from a solvent, conversion into an acid addition compound or column chromatography.

Those starting compounds of the general formula II which are not already known can be prepared as follows:

An appropriately substituted acetophenone is condensed with a benzaldehyde to give an α,β-unsaturated ketone in a manner which is known from the literature, such as, for example, by the method described in *Org. Reactions* Volume 16, page 1 et seq., John Wiley Verlag, New York, 1968, in Houben-Weyl, *Methoden der organischen Chemie,* Volume 7/2b, page 1457 et seq. G. Thieme Verlag, Stuttgart, 1976 or in *Chem. Ber.* 94 (1961), 26. This ketone is subjected to catalytic hydrogenation to give the corresponding 2-hydroxy-β-phenyl-propiophenone, also in a manner which is known from the literature, for example as described in R. N. Rylander, "Catalytic Hydrogenation over Pt-Metals", page 282, Academic Press 1967.

This 2-hydroxy-β-phenyl-propiophenone is converted into a propiophenone of the formula II by alkylation with an epihalogenohydrin or a 1,3-dihalogeno-propan-2-ol in a conventional manner.

Suitable epihalogenohydrins include epichlorohydrin, epibromohydrin and epiiodohydrin, and particularly suitable 1,3-dihalogeno-propan-2-ols include 1,3-dichloro-propan-2-ol and 1,3-dibromo-propan-2-ol.

The reaction of the 2-hydroxy-β-phenyl-propiophenone for the preparation of the compound of the formula II is carried out at from 50° to 80° C., under atmospheric or superatomospheric pressure, in an inert diluent or solvent, e.g. acetone, methanol or dimethylformamide, in the presence of a base, e.g. potassium carbonate, as an acid acceptor.

The 2-hydroxy-β-phenyl-propiophenones and the starting compounds II can in some cases be used directly in the subsequent reaction step without prior purification.

Process (b) is successfully carried out in alcoholic solution. Particularly suitable catalysts are noble metal catalysts, e.g. palladium, on charcoal.

The compounds of the formula I according to the invention have a chirality center on carbon atom 2 of the aliphatic side chain, and are obtained as racemates which can be resolved into the optically active antipodes in a conventional manner, for example by formation of a diastereomeric salt with an optically active auxiliary acid, e.g. dibenzoyltartaric acid, camphor-10-sulfonic acid, ditoluyltartaric acid or 3-bromo-camphor-8-sulfonic acid.

If appropriate, the resulting compound according to the invention is converted into an acid addition salt of a physiologically acceptable acid. Examples of the usual physiologically acceptable inorganic or organic acids include hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Further examples can be found in *Fortschritte der Arzneimittelforschung* Volume 10, pages 224–225, Birkhauser Verlag, Basle and Stuttgart, 1966.

The acid addition salts are as a rule obtained in a conventional manner by mixing the free base or a solution thereof with the corresponding acid or a solution thereof in an organic solvent, e.g. a lower alcohol, such as methanol, ethanol or propanol, a lower ketone, such as acetone, methyl ethyl ketone or methyl isobutyl ketone, or an ether, such as diethyl ether, tetrahydrofuran or dioxane. For better crystallization, mixtures of the above solvents can also be used. Moreover, a pharmaceutically acceptable aqueous solution of an acid addition compound of an aminopropanol derivative of the formula I can be prepared by dissolving the free base in an aqueous acid solution.

Because of their antiarrhythmic, β-sympatholytic and Ca-antagonistic properties, the compounds according to the invention and their physiologically acceptable acid addition salts are particularly suitable for the pharmacotherapy of cardiac irregularity and for the prophylaxis of sudden cardiac death, as well as for the treatment of coronary heart disease.

The antiarrhythmic activity of the compounds according to the invention was determined on the isolated left atrium of male guineapigs (strain: Pirbright white, weight: 350 to 450 g).

Atria suspended in an organ bath (volume: 125 ml) with carbogen-saturated Tyrode's solution (pH 7.4, 32° C.) were pre-loaded with 1.0 g and subjected to square-wave pulses having a base rhythm of 1 Hz and twice the excitation threshold (rheobase: 0.2–1.4 V, chronaxia: 0.3–0.5 msec).

The frequency (Hz) up to which contraction follows each stimulus (maximum rhythmicity, MR) was determined, by automatically and continuously increasing the frequency, as a criterion of the antiarrhythmic activity. The concentration which causes a drop in the maximum rhythmicity of 50% (EC 50%) was calculated from the linear relationship between the logarithm of the concentration (mg/l) and the relative drop in the maximum rhythmicity (%).

Moreover, the novel compounds were administered orally or intravenously to male rats (strain: Sprague Dawley, weight: 200–230 g) to determine the antiarrhythmic activity. 45 minutes later, the animals were anesthetized by intraperitoneal administration of 100 mg/kg of thiobutabarbital sodium. Aconitine served as the arrhythmogenic substance, and was infused intravenously at a dosage rate of 0.005 mg/kg/minute 60 minutes after administration of the substance. In untreated animals (n=52), arrhythmias appeared in the ECG after 2.74±0.07 minutes. These arrhythmias can be delayed by antiarrhythmic drugs, as a function of the dose.

The dose which extends the infusion period by 50% (ED 50%) was determined from the linear relationship between the logarithm of the dose (mg/kg) of the trial substance and the relative extension of the period of aconitine infusion (Δ %).

The known antiarrhythmic drup propafenone [2-(2-hydroxy-3-propylamino-propoxy)-3-phenyl-propiophenone hydrochloride] was used as the comparative substance.

On the isolated guineapig atrium (Table 1) the compounds according to the invention effect a drop in the MR which is 3 times that caused by propafenone. A powerful to very powerful antiarrhythmic action, in comparison with propafenone, was also found in the model of aconitine arrhythmia in rats (Table 2). The tolerance of the compounds according to the invention in this test is good. Thus, the toxic dose is much higher than the dose which causes an antiarrhythmic effect.

TABLE 1

Antiarrhythmic action on the isolated guineapig atrium

| Substance of Example No. | Maximum rhythmicity (ED 50% mg/l[1]) |
| --- | --- |
| 1 | 1.90 |
| 2 | 0.874 |
| 3 | 1.51 |
| 6 | 1.71 |
| 7 | 1.66 |
| 9 | 0.757 |
| 10 | 1.13 |
| 12 | 1.25 |
| 14 | 2.17 |
| 15 | 0.728 |
| 18 | 1.30 |
| 22 | 1.21 |
| 23 | 1.64 |
| 24 | 2.65 |
| 25 | 1.01 |
| 29 | 1.71 |
| 33 | 2.05 |
| 34 | 1.72 |
| 35 | 1.65 |
| 46 | 0.778 |
| 47 | 1.45 |
| 48 | 0.923 |
| 49 | 1.82 |
| 55 | 0.854 |
| 57 | 2.04 |
| 58 | 1.92 |
| 60 | 1.82 |
| 64 | 1.36 |
| 67 | 0.658 |
| Propafenone | 2.02 |

[1]Concentration (mg/l) which causes a 50% drop in the maximum rhythmicity

TABLE 2

Antiarrhythmic action on aconitine arrhythmia in rats (peroral administration)

| Substance from Example No. | ED 50% mg/kg[1] |
| --- | --- |
| 1 | 15 |
| 2 | 46.4 |
| 3 | 38.2 |
| 4 | 46.4 |
| 8 | 21 |
| 9 | 27 |
| 10 | 46.4 |
| 16 | 29 |
| 23 | 31.6 |
| 24 | 25.4 |
| 25 | 11.2 |
| 33 | 24.5 |
| 34 | 21.5 |
| 35 | 1.99 |
| 36 | 6.92 |
| 37 | 46.4 |
| 38 | 21.5 |
| 40 | 46.4 |
| 49 | 31.6 |
| 55 | 5.70 |
| 56 | 3.40 |
| 57 | 1.78 |
| 58 | 2.33 |
| 59 | 21.5 |

TABLE 2-continued

Antiarrhythmic action on aconitine arrhythmia in rats (peroral administration)

| Substance from Example No. | ED 50% mg/kg[1] |
| --- | --- |
| 60 | 3.25 |
| 61 | 1.90 |
| 62 | 21.5 |
| 63 | 3.03 |
| 66 | 21.5 |
| 67 | 2.15 |
| 68 | 46.4 |
| 69 | 31.6 |
| 71 | 0.510[2] |
| Propafenone | 58.7[2] |
| | 0.724[2] |

[1]Dose (mg/kg) which causes a 50% extension in the period of aconitine infusion
[2]Intravenous administration The novel compounds can be administered orally or intravenously in a conventional manner. The dosage depends on the age, condition and weight of the patient and on the mode of administration. As a rule, the daily dose of active compound is from about 5 to 75 mg/kg of body weight in the case of oral administration, and from about 1 to 10 mg/kg of body weight in the case of parenteral administration.

The novel compounds may be employed in the conventional solid or liquid pharmaceutical forms, for example as tablets, film tablets, capsules, powders, granules, dragees, suppositories or solutions. These are prepared in a conventional manner, and to do so the active compounds can be mixed with the conventional pharmaceutical auxiliaries, such as tablet binders, fillers, preservatives, tablet disintegrants, flow control agents, plasticizers, wetting agents, dispersants, emulsifiers, solvents, retardants and/or antioxidants (cf. H. Sucker et al.: Pharmazeutische Technologie, Thieme-Verlag, Stuttgart, 1978). The administration forms thus obtained normally contain from 1 to 99 percent by weight of the active compound.

The Examples illustrate the invention.

(A) Preparation of the starting compounds

Example I

3-Oxo-1-phenyl-3-(2'-hydroxy-5'-chloro-phenyl)-propene 34.1 g of 5-chloro-2-hydroxyacetophenone and 22 g of benzaldehyde were added to a mixture of 180 ml of $H_2O$ and 37 g of 50% strength sodium hydroxide solution at room temperature. The mixture was heated to 55°–60° C., with thorough stirring, and was stirred at this temperature for about 1 hour. It was then rendered weakly acid with 25% strength $H_2SO_4$ (about 100 ml), with thorough cooling, and the precipitate was filtered off with suction, washed thoroughly with $H_2O$ and recrystallized from a 9:1 mixture of methanol and acetone to give 38.7 g of 3-oxo-1-phenyl-3-(2'-hydroxy-5'-chlorophenyl)-propene of melting point 88°–90° C.

The following compounds were prepared in a similar manner: 3-oxo-1-(4'-methoxyphenyl)-3-(2'-hydroxyphenyl)-propene of melting point 91°–92° C.; 3-oxo-1-(2',4'-dichlorophenyl)-3-(2'-hydroxyphenyl)-propene of melting point 169°–172° C.; 3-oxo-1-(2'-methoxyphenyl)-3-(2'-hydroxyphenyl)-propene of melting point 110°–112° C.; 3-oxo-1-(3',4'-dimethoxyphenyl)-3-(2'-hydroxyphenyl)-propene of melting point 114°–116° C.; 3-oxo-1-(3',4',5'-trimethoxyphenyl)-3-(2'-hydroxyphenyl)-propene of melting point 152°–153° C.; 3-oxo-1-(4'-dimethylaminophenyl)-3-(2'-hydroxyphenyl)-propene of melting point 174°–176° C.; 3-oxo-1-(4'-chlorophenyl)-3-(2'-hydroxyphenyl)-propene of melting point 149°–150° C.; 3-oxo-1-(4'-methylphenyl)-3-(2'-hydroxyphenyl)-propene of melting point 118°–120° C.; 3-oxo-1-(4'-fluorophenyl)-3-(2'-hydroxyphenyl)-propene of melting point 115°–119° C.; 3-oxo-1-(3',4'-dimethoxyphenyl)-3-(2'-hydroxy-5'-methylphenyl)-propene of melting point 142°–145° C.; 3-oxo-1-(4'-chlorophenyl)-3-(2'-hydroxy-5'-methylphenyl)-propene of melting point 151°–156° C.; 3-oxo-1-(4'-methoxyphenyl)-3-(2'-hydroxy-5'-chlorophenyl)-propene of melting point 108°–111° C.; 3-oxo-1-(4'-fluorophenyl)-3-(2'-hydroxy-5'-chlorophenyl)-propene of melting point 183°–185° C.; 3-oxo-1-(4'-diethylaminophenyl)-3-(2'-hydroxyphenyl)-propene of melting point 117°–119° C.; 3-oxo-1-(4'-dimethylaminophenyl)-3-(2'-hydroxy-5'-chlorophenyl)-propene of melting point 159°–162° C. and 3-oxo-1-(4'-dimethylaminophenyl)-3-(2'-hydroxy-5'-methylphenyl)-propene of melting point 125°–129° C.

EXAMPLE II (a) 2-Hydroxy-5-chloro-β-phenyl-propiophenone 25 g (0.097 mole) of 3-oxo-1-phenyl-3-(2'-hydroxy-5'-chlorophenyl)-propene were dissolved in 200 ml of tetrahydrofuran and were hydrogenated under atmospheric pressure at from 40° to 50° C. in the presence of 1.5 g of a catalyst (0.5% Pd-on-Al$_2$O$_3$). After from 2 to 3 hours, the uptake of hydrogen had ended (2,100 ml). The catalyst was then filtered off and the filtrate was freed from the solvent by distillation under reduced pressure. The residue which remained was recrystallized from methanol. Yield: 19.9 g, melting point: 56°–57° C.

The following compounds were prepared in a similar manner: 2-hydroxy-β-(4-methoxyphenyl)-propiophenone of melting point 51°–54° C.; 2-hydroxy-β-(2,4-dichlorophenyl)-propiophenone of melting point 106° C.; 2-hydroxy-β-(4-dimethylaminophenyl)-propiophenone of melting point 69°–71° C.; 2-hydroxy-β-(3,4-dimethoxyphenyl)-propiophenone of melting point 84°–87° C.; 2-hydroxy-β-(4-dimethylaminophenyl)-propiophenone of melting point 62° C.; 2-hydroxy-β-(4-diethylaminophenyl)-propiophenone of melting point 49°–51° C.; 2-hydroxy-5-methyl-β-(4-dimethylaminophenyl)-propiophenone of melting point 90°–92° C. and 2-hydroxy-5-chloro-β-(4-dimethylaminophenyl)-propiophenone of melting point 99° C.; 2-hydroxy-β-(4-chlorophenyl)-propiophenone, C$_{15}$H$_{13}$ClO$_2$ (260.72); oily: calculated: C: 69.10; H; 5.03; Cl: 13.60; found: C: 69.5; H: 5.4; Cl: 13.2; and 2-hydroxy-β-(2-methoxyphenyl)-propiophenone, C$_{16}$H$_{16}$O$_3$ (256.30); oily: calculated: C: 74.98; H: 6.29; found: C: 74.7; H: 6.4.

The other propiophenones were used without further purification.

EXAMPLE III

2-Hydroxy-4-methoxy-β-phenyl-propiophenone 16.6 g (100 mmoles) of 2-hydroxy-4-methoxy-acetophenone and 10.6 g (100 mmoles) of benzaldehyde were dissolved in 300 ml of methanol, and 8 g (200 mmoles) of sodium hydroxide dissolved in 30 ml of H$_2$O were added dropwise. The solution turned yellow. The reaction product was stirred at room temperature for 72 hours and the mixture was then diluted with 200 ml of methanol and about 2 g of 5% Pd-on-C were added. The yellow solution was hydrogenated. The hydrogen uptake was 1,800 ml. The suspension was filtered and the mother liquor was brought to pH 5 with about 10 ml of concentrated acetic acid. Crystals precipitated and were filtered off with suction. Yield: 18 g (=70.2%); melting point: 100° C.

EXAMPLE IV 2-(2',3'-Epoxypropoxy)-5-chloro-β-phenyl-propiophenone 62 g (0.265 mole) of 2-hydroxy-5-chloro-β-phenyl-propiophenone, 125.4 g (0.915 mole) of epibromohydrin, 70 ml of dimethylformamide and 48.7 g (0.353 mole) of anhydrous K$_2$CO$_3$ were stirred thoroughly at 60° C. for 5 hours. When the mixture had cooled, 250 ml of H$_2$O were added and the organic phase was freed from excess epibromohydrin by distillation under reduced pressure. The residue which remained was recrystallized from cyclohexane/methyl tert.-butyl ether. Yield: 67 g (=79%); melting point: 46°–47° C.

The following compound was prepared in a similar manner: 2-(2',3'-epoxypropoxy)-5-chloro-β-(4-dimethylaminophenyl)-propiophenone of melting point 93°–95° C.

All the other starting materials were prepared in a similar manner, but were reacted without further purification.

EXAMPLE V

3-Oxo-1-phenyl-3-[(2'-hydroxy-3'-n-propylamino-propoxy)-4-benzyloxy-phenyl]-propene (a) 2-Hydroxy-4-benzyloxy-acetophenone 15.2 g (100 mmoles) of 2,4-dihydroxy-acetophenone, 17.1 g (100 mmoles) of benzyl bromide and 13.8 g (100 mmoles) of potassium carbonate in 150 ml of acetone were refluxed, with stirring, for 8 hours, during which the mixture changed from violet to reddish brown. When the mixture had cooled, the solvent was distilled off, the residue was taken up in 100 ml of ethyl acetate and the mixture was extracted by shaking with 100 ml of 1 N sodium hydroxide solution. The phases were separated and the organic phase was acidified with 110 ml of 1 N HCl. The phases were separated again and the organic phase was dried over sodium sulfate. The drying agent was filtered off and the solvent was distilled off to give a crude yield of 20.5 g. The crude product was recrystallized from 180 ml of ethanol. Yield: 17.5 g; melting point: 108°–109° C.

(b) 3-Oxo-1-phenyl-3-(2'-hydroxy-4-benzyloxyphenyl)-propene 17.63 g (72.6 mmoles) of 2-hydroxy-4-benzyloxy-acetophenone, 17.60 g (165.8 mmoles) of benzaldehyde and 35.20 g of 50% strength sodium hydroxide solution in 200 ml of ethanol were stirred for 3 days, during which crystals precipitated. The crystal sludge was acidified with 100 ml of 5 N hydrochloric acid and was stirred for 10 minutes. The mixture was filtered with suction to give 40.0 g of moist crystals. The crude product was recrystallized from 800 ml of ethanol. Yield: 13.6 g; melting point: 116°–118° C.

(c) 3-Oxo-1-phenyl-3-[2'-(2'',3''-epoxypropoxy)-4'-benzyloxyphenyl]-propene 13.55 g (41.0 mmoles) of 3-oxo-1-phenyl-3-(2'-hydroxy-4-benzyloxy-phenyl)-propene and 1.64 g (41.0 mmoles) of sodium hydroxide in 200 ml of epichlorohydrin were refluxed for 4 hours, during which the water of reaction formed was removed. The reaction was then cooled and the sodium chloride formed was filtered off with suction. The filtrate was concentrated in vacuo. The residue was used in the next stage without being purified.

(d)
3-Oxo-1-phenyl-3-[(2'-hydroxy-3'-n-propylamino-propoxy)-4-benzyloxy-phenyl]-propene 16.3 g (42.2 mmoles) of 3-oxo-1-phenyl-3-[2'-(2'',3''-epoxypropoxy)-4'-benzyloxy-phenyl]-propene in 200 ml of n-propylamine were refluxed for 4 hours. The excess amine was then distilled off and the resulting crude product was used directly, without further purification, for the preparation of the end product according to the invention.

The following compound was prepared in a similar manner: 3-oxo-1-phenyl-3-[(2'-hydroxy-3'-n-propylaminopropoxy)-5-benzyloxy-phenyl]-propene (B) Preparation of the compounds according to the invention:

EXAMPLE 1

2-[2'-Hydroxy-3'-(4-hydroxybut-2-ylamino)-propoxy]-β-phenyl-propiophenone hydrochloride 5 g of 2-(2',3'-epoxypropoxy)-β-phenyl-propiophenone and 1.55 g of 4-hydroxy-but-2-ylamine were dissolved in 100 ml of isopropanol and the solution was refluxed on a waterbath for 8 hours. After the mixture had been cooled, the solvent was distilled off under reduced pressure, and 5.5 g of oily residue remained. The crude product was purified over a silica gel column (eluant: a 70:30 mixture of toluene and methanol) and the pure fractions were converted into the hydrochloride. Yield: 2.9 g (40.5%); melting point: 88.5° C. (acetone/ether).

EXAMPLE 2

2-[2'-Hydroxy-3'-(3-methoxyprop-2-ylamino)-propoxy]-β-phenyl-propiophenone hydrochloride 10 g (0.035 mole) of 2-(2',3'-epoxypropoxy)-β-phenyl-propiophenone and 16 g (0.18 mole) of 3-methoxyprop-2-ylamine were dissolved in 150 ml of isopropanol and the solution was refluxed on a waterbath for 6 hours. The solvent was then distilled off under reduced pressure. The hydrochloride was prepared from the 12.85 g of oily residue with the aid of ethereal hydrochloric acid and was recrystallized from acetone/ether. Yield: 9.8 g (68%); melting point: 119° C.

The following compounds were prepared in a similar manner:

3. 2-(2'-Hydroxy-3'-cyclopropylamino-propoxy)-β-phenyl-propiophenone hydrochloride of melting point 153° C.
4. 2-(2'-Hydroxy-3'-cyclohexylamino-propoxy)-β-phenyl-propiophenone hydrochloride of melting point 162° C.
5. 2-(2'-Hydroxy-3'-allylamino-propoxy)-β-phenyl-propiophenone hydrochloride of melting point 153° C.
6. 2-[2'-Hydroxy-3'-(1-butyn-3-ylamino)-propoxy]-β-phenyl-propiophenone hydrochloride of melting point 133° C.
7. 2-[2'-Hydroxy-3'-(3-methyl-1-butyn-3-ylamino)-propoxy]-β-phenyl-propiophenone hydrochloride of melting point 131°–132° C.
8. 2-[2'-Hydroxy-3'-(3-hydroxy-3-methyl-butylamino)-propoxy]-β-phenyl-propiophenone hydrochloride of melting point 145°–146° C.
9. 2-[2'-Hydroxy-3'-(2-methoxyethylamino)-propoxy]-β-phenyl-propiophenone hydrochloride of melting point 112°–113° C.
10. 2-[2'-Hydroxy-3'-(3-thiomethoxyprop-2-ylamino)-propoxy]-β-phenyl-propiophenone hydrochloride of melting point 119° C.
11. 2-[2'-Hydroxy-3'-(2-phenethylamino)-propoxy]-β-phenyl-propiophenone hydrochloride of melting point 157°–158° C.
12. 2-[2'-Hydroxy-3'-(2-phenylpropylamino)-propoxy]-β-phenyl-propiophenone hydrochloride of melting point 152° C.
13. 2-[2'-Hydroxy-3'-(1-methylbenzylamino)-propoxy]-β-phenyl-propiophenone hydrochloride of melting point 119°–120° C.
14. 2-[2'-Hydroxy-3'-(2-(3,4-dimethoxyphenyl)-ethylamino)-propoxy]-β-phenyl-propiophenone hydrochloride of melting point 129° C.
15. 2-[2'-Hydroxy-3'-[N-methyl-N-(2-(3,4-dimethoxyphenyl)ethylamino)]-propoxy]-β-phenyl-propiophenone hydrochloride of melting point 121° C.
16. 2-[2'-Hydroxy-3'-(2-dimethylaminoethylamino)-propoxy]-β-phenyl-propiophenone bis-hydrochloride of melting point 136°–137° C.
17. 2-[2'-Hydroxy-3'-(3-dimethylaminopropylamino)-propoxy]-β-phenyl-propiophenone bis-hydrochloride of melting point 150°–151° C.
18. 2-[2'-Hydroxy-3'-(N,N-dimethylamino)-propoxy]-β-phenyl-propiophenone hydrochloride of melting point 154° C.
19. 2-[2'-Hydroxy-3'-(N,N-diisopropylamino)-propoxy]-β-phenyl-propiophenone hydrochloride of melting point 131° C.
20. 2-(2'-Hydroxy-3'-piperidino-propoxy)-β-phenyl-propiophenone hydrochloride of melting point 155°–156° C.
21. 2-(2'-Hydroxy-3'-morpholino-propoxy)-β-phenyl propiophenone hydrochloride of melting point 153° C.
22. 2-[2'-Hydroxy-3'-(3-phenyl-pyrrolidino)-propoxy]-β-phenyl-propiophenone hydrochloride of melting point 128°–130° C.
23. 2-[2'-Hydroxy-3'-(4-hydroxypiperidino)-propoxy]-β-phenyl-propiophenone hydrochloride of melting point 150°–152° C.
24. 2-[2'-Hydroxy-3'-(4-hydroxy-4-phenyl-piperidino)-propoxy]-β-phenyl-propiophenone hydrochloride of melting point 107°–108° C.
25. 2-[2'-Hydroxy-3'-(4-methyl-piperazin-1-yl)-propoxy]-β-phenyl-propiophenone bis-hydrochloride of melting point 152°–153° C.
26. 2-{2'-Hydroxy-3'-[4-(2-methoxyphenyl)-piperazin-1-yl]-propoxy}-β-phenyl-propiophenone of melting point 119°–120° C.
27. 2-{2'-Hydroxy-3'-[4-(4-fluorophenyl)-piperazin-1-yl]-propoxy}-β-phenyl-propiophenone of melting point 93° C.
28. 2-{2'-Hydroxy-3'-[2-(2-methylphenyl)propylamino]-propoxy}-β-phenyl-propiophenone hydrochloride of melting point 140°–141° C.
29. 2-(2'-Hydroxy-3'-n-propylamino-propoxy)-β-(2-methoxyphenyl)-propiophenone hydrochloride of melting point 123° C.

30. 2-(2'-Hydroxy-3'-n-propylamino-propoxy)-β-(4-methoxyphenyl)-propiophenone hydrochloride of melting point 159° C.
31. 2-(2'-Hydroxy-3'-n-propylamino-propoxy)-β-(4-chlorophenyl)-propiophenone hydrochloride of melting point 157° C.
32. 2-(2'-Hydroxy-3'-n-propylamino-propoxy)-β-(2,4-dichlorophenyl)-propiophenone hydrochloride of melting point 119°–123° C.
33. 2-(2'-Hydroxy-3'-n-propylamino-propoxy)-β-(4-fluorophenyl)-propiophenone hydrochloride of melting point 144° C.
34. 2-(2'-Hydroxy-3'-n-propylamino-propoxy)-β-(4-methylphenyl)-propiophenone hydrochloride of melting point 148°–149° C.
35. 2-(2'-Hydroxy-3'-n-propylamino-propoxy)-β-(4-dimethylaminophenyl)-propiophenone hydrochloride of melting point 165°–166° C.
36. 2-(2'-Hydroxy-3'-n-propylamino-propoxy)-β-(3,4-dimethoxyphenyl)-propiophenone hydrochloride of melting point 185°–186° C.
37. 2-(2'-Hydroxy-3'-n-propylamino-propoxy)-5-chloro-β-phenyl-propiophenone hydrochloride of melting point 163°–164° C.
38. 2-[2'-Hydroxy-3'-(3-methoxy-prop-2-ylamino)-propoxy]-5-chloro-β-phenyl-propiophenone hydrochloride of melting point 105°–106° C.
39. 2-(2'-Hydroxy-3'-cyclopropylamino-propoxy)-5-chloro-β-phenyl-propiophenone hydrochloride of melting point 152° C.
40. 2-(2'-Hydroxy-3'-piperidino-propoxy)-5-chloro-β-phenyl-propiophenone of melting point 91°–92° C.
41. 2-[2'-Hydroxy-3'-(2-(3,4-dimethoxyphenyl)-ethylamino)-propoxy]-5-chloro-β-phenyl-propiophenone hydrochloride of melting point 137°–141° C.
41. 2-[2'-Hydroxy-3'-[N-methyl-N-2-(3,4-dimethoxyphenyl)-ethylanino)]-propoxy]-5-chloro-≈-phenyl-propiophenone hydrochloride of melting point 135° C.
43. 2-[2'-Hydroxy-3'-(4-hydroxy-4-phenyl-piperidino)-propoxy]-5-chloro-β-phenyl-propiophenone hydrochloride of melting point 214°–216° C.
44. 2-(2'-Hydroxy-3'-n-propylamino-propoxy)-5-chloro-β-(4-methoxy-phenyl)-propiophenone hydrochloride of melting point 165°–167° C.
45. 2-(2'-Hydroxy-3'-n-propylamino-propoxy)-5-methyl-β-(4-chlorophenyl)-propiophenone hydrochloride of melting point 134°–135° C.
46. 2-(2'-Hydroxy-3'-di-n-propylamino-propoxy)-5-methyl-β-(4-chlorophenyl)-propiophenone hydrochloride of melting point 119°–123° C.;
47. 2-(2'-Hydroxy-3'-di-n-propylamino-propoxy)-5-chloro-β-(p-fluorophenyl)-propiophenone hydrochloride of melting point 139°–144° C.
48. 2-(2'-Hydroxy-3'-n-propylamino-propoxy)-5-methyl-β-(3,4-dimethoxyphenyl)-propiophenone hydrochloride of melting point 132°–133° C.
49. 2-(2'-Hydroxy-3'-n-propylaminopropoxy)-β-(3,4,5-trimethoxyphenyl)-propiophenone of melting point 197°–198° C.
50. 2-[2'-Hydroxy-3'-(2-hydroxyethylamino)-propoxy]-5-chloro-β-phenyl-propiophenone of melting point 99°–103° C.
51. 2-(2'-Hydroxy-3'-aminopropoxy)-β-phenyl-propiophenone oxalate of melting point 149°–151° C.
52. 2-(2'-Hydroxy-3'-methylaminopropoxy)-β-phenyl-propiophenone hydrochloride of melting point 141°–143° C.
53. 2-(2'-Hydroxy-3'-ethylamino-propoxy)-β-phenyl-propiophenone hydrochloride of melting point 162°–164° C.
54. 2-(2'-Hydroxy-3'-n-propylamino-propoxy)-4-methoxy-β-phenyl-propiophenone hydrochloride of melting point 174°–177° C.

EXAMPLE 55

2-(2'-Hydroxy-3'-piperidino-propoxy)-β-(4-dimethylaminophenyl)-propiophenone 8 g (0.025 mole) of 2-(2',3'-epoxypropoxy)-β-(4-dimethylaminophenyl)-propiophenone and 20 ml of piperidine were dissolved in 100 ml of isopropanol and the solution was kept on a waterbath for 6 hours. The solvent and excess amine were then distilled off under reduced pressure. 9 g of oily residue remained, and were crystallized from a little absolute ethanol, with the addition of active charcoal. Yield: 3.15 g (31%), melting point: 113°–115° C.

EXAMPLE 56

2-(2'-Hydroxy-3'-isopropylamino-propoxy)-β-(4-dimethylaminophenyl)-propiophenone hydrochloride.

8 g of 2-(2',3'-epoxypropoxy)-β-(4-dimethylaminophenyl)-propiophenone and 13 ml of isopropylamine in isopropanol were reacted by a procedure similar to that in Example 55. The residue which remained after conventional working-up was dissolved in 150 ml of acetone, and 4.6 ml of ethereal HCl (about 5 N) were added. The crystals were filtered off with suction and recrystallized again from acetone. Yield: 3.8 g (36.5%), melting point: 149° C.

The following compounds were prepared in a similar manner:

57. 2-(2'-Hydroxy-3'-cyclopropylamino-propoxy)-β-(4-dimethylaminophenyl)-propiophenone hydrochloride of melting point 128°–133° C.
58. 2-(2'-Hydroxy-3'-n-butylamino-propoxy)-β-(4-dimethylaminophenyl)-propiophenone hydrochloride of melting point 161°–163° C.
59. 2-[2'-Hydroxy-3'-(2-hydroxyethylamino)-propoxy]-β-(dimethylaminophenyl)-propiophenone hydrogen oxalate of melting point 138° C.
60. 2-[2'-Hydroxy-3'-(3-methoxy-prop-2-ylamino)-propoxy]-β-(4-dimethylaminophenyl)-propiophenone hydrochloride of melting point 134°–135° C.
61. 2-[2'-Hydroxy-3'-n-propylamino-propoxy)-β-(4-diethylaminophenyl)-propiophenone hydrochloride of melting point 154°–155° C.
62. 2-(2'-Hydroxy-3'-n-propylamino-propoxy)-5-chloro-β-(4-dimethylaminophenyl)-propiophenone hydrochloride of melting point 166°–167° C.
63. 2-(2'-Hydroxy-3'-n-propylamino-propoxy)-5-methyl-β-(4-dimethylaminophenyl)-propiophenone hydrochloride of melting point 161°–162° C.
64. 2-[2'-Hydroxy-3'-(N,N-diisopropylamino)-propoxy]-β-(4-dimethylaminophenyl)-propiopheone hydrochloride of melting point 143°–144° C.
65. 2-[2'-Hydroxy-3'-(N,N-diisopropylamino)-propoxy]-5-methyl-β-(4-dimethylaminophenyl)-propiophenone hydrochloride of melting point 143°–145° C.
66. 2-[2'-Hydroxy-3'-(N,N-diisopropylamino)-propoxy]-5-chloro-β-(4-dimethylaminophenyl)-propiophenone hydrochloride of melting point 148°–150° C.
67. 2-[2'-Hydroxy-3'-(4-methyl-piperazin-1-yl)-propoxy]-β-(4-dimethylaminophenyl)-propiophenone hydrochloride of melting point 129° C.

68. 2-[2'-Hydroxy-3'-(4-methyl-piperazin-1-yl)-propoxy]-5-methyl-β-(4-dimethylaminophenyl)-propiophenone hydrochloride of melting point 169°–170° C.

69. 2-[2'-Hydroxy-3'-(3-methoxy-prop-2-ylamino)-propoxy]-5-methyl-β-(4-dimethylaminophenyl)-propiophenone hydrochloride of melting point 121°–124° C.

EXAMPLE 70

2-(2'-Hydroxy-3'-n-propylamino-propoxy)-4-hydroxy-β-phenyl-propiophenone hydrochloride 1 g of 5% Pd-on-C was added to the product obtained in Example 5, and the mixture was dissolved in 150 ml of methanol. Hydrogenation was then carried out until 1,830 ml of hydrogen had been taken up. The catalyst was then filtered off and the solvent was distilled off. 15.8 g of a red viscous oil were obtained, and were refluxed with 100 ml of 1 N hydrochloric acid for 1 hour. The oil, which did not dissolve, was separated off. The crystals formed after cooling were filtered off with suction and recrystallized twice from 150 ml of a 1:2 mixture of ethanol and acetone. Yield: 2.7 g; melting point: 146°–148° C.

The following compound was prepared in a similar manner:

71. 2-(2'-Hydroxy-3'-n-propylamino-propoxy)-5-hydroxy-β-phenyl-propiophenone hydrochloride of melting point 220°–221° C.

We claim:

1. 2-(2'-Hydroxy-3'-n-propylamino-propoxy)-β-(3,4-dimethoxyphenyl)-propiophenone or a physiologically acceptable acid addition salt thereof.

2. A therapeutic composition for treating cardiac arrhythmias and cornary insufficiency comprising a pharmaceutical excipient and an effective amount of the aminopropanol derivative of claim 1.

3. The method of treating cardiac arrhythmias and coronary insufficiency in a patient suffering therefrom, which comprises administering to the patient an effective amount of the aminopropanol derivative of claim 1.

4. 2-(2'-Hydroxy-3'-n-propylamino-propoxy)-5-hydroxy-β-phenyl-propiophenone or a physiologically acceptable acid addition salt thereof.

5. A therapeutic composition for treating cardiac arrhythmias and coronary insufficiency comprising a pharmaceutical excipient and an effective amount of the aminopropanol derivative defined in claim 4.

6. The method of treating cardiac arrhythmias and coronary insufficiency in a patient suffering therefrom which comprises administering an effective amount of the aminopropanol derivative defined in claim 4.

* * * * *